United States Patent [19]

Fleming

[11] Patent Number: 4,789,639

[45] Date of Patent: Dec. 6, 1988

[54] LIQUID RECOVERY DEVICE

[75] Inventor: Beverly M. Fleming, Raleigh, N.C.

[73] Assignee: Becton, Dickinson and Company, Franklin Lakes, N.J.

[21] Appl. No.: 58

[22] Filed: Jan. 2, 1987

[51] Int. Cl.⁴ .............. C12M 1/30; B01L 3/00; A61M 35/00

[52] U.S. Cl. .................. 436/178; 436/810; 422/61; 422/100; 422/102; 435/295; 604/1; 206/361; 206/569

[58] Field of Search ............ 128/759; 422/61, 100, 422/102; 436/178, 810; 435/292, 294, 295; 604/1, 2; 206/361, 15.2, 15.3, 569

[56] References Cited

U.S. PATENT DOCUMENTS

| | | | |
|---|---|---|---|
| 3,368,549 | 2/1968 | Barr et al. | 435/295 |
| 3,954,563 | 5/1976 | Mennen | 435/295 |
| 4,175,008 | 11/1979 | White | 435/295 |
| 4,209,488 | 6/1980 | Breno | 422/101 |
| 4,358,425 | 11/1982 | Finney et al. | 422/102 |
| 4,409,988 | 10/1983 | Greenspan | 435/295 |
| 4,652,429 | 3/1987 | Konrad | 422/102 |
| 4,657,869 | 4/1987 | Richards et al. | 435/295 |

FOREIGN PATENT DOCUMENTS

1937021 7/1969 Fed. Rep. of Germany .

Primary Examiner—Barry S. Richman
Assistant Examiner—Lynn M. Kummert
Attorney, Agent, or Firm—Richard E. Brown

[57] ABSTRACT

A liquid recovery device includes a receptacle, a swab for transferring a sample to a liquid in the receptacle, and a wringing unit to remove the liquid from the swab after the sample is transferred. The wringing unit has a sleeve with a closure in one end. A shaft of the swab extends through a passageway in the closure. When the swab in the receptacle is raised by upward movement of the shaft, an absorbent pad on the lower end of the shaft enters the passageway and is compressed. The compression of the pad wrings liquid therefrom which drips back into the receptacle. The device may be used in a method to prepare solutions of the sample in a minimum amount of liquid.

1 Claim, 7 Drawing Sheets

LIQUID RECOVERY DEVICE

BACKGROUND OF THE INVENTION

1. Field of the Invention

The present invention relates to preparation of solutions for analysis, and more particularly, related to a device and method for recovery of a solution from an absorbent material.

2. Background of the Invention

Immunoassay is conventionally carried out by contacting in an assay vehicle a solution of an analyte, such as an antigen, antibody or hapten, with a specific antianalyte. The sensitivity of the assay is often at least in part determined by the concentration of the analyte in the assay vehicle, and, in general, it is advantageous to carry out the assay on as concentrated a solution of analyte as possible.

When a bacterial or viral infection is suspected in a patient, identification of the pathogen is often necessary in order to determine the most effective treatment. Frequently this entails taking a culture sample, by swabbing the patient's throat or nasal passage, immersing the swab in an appropriate liquid in a receptacle to give a solution of an antigen associated with the pathogen, and performing an immunoassay on the solution. Use of too much liquid for immersion of the swab reduces the antigen concentration in the solution. On the other hand, use of too little liquid results in absorption of a substantial portion of the solution into the swab so that insufficient solution remains in the receptacle to perform the assay.

A variety of related devices has been disclosed for collecting, maintaining and transporting culture specimens to be taken by swab. In general, these devices include a swab and a receptacle containing a liquid to keep the specimen viable during transport, and may also include structure to protect a technician from coming into contact with the specimen at any time during use of the device. Representative of such devices are those disclosed in U.S. Pat. No. 3,674,007 to Freis and U.S. Pat. No. 3,776,220 to Monaghan. In some such devices, as exemplified by U.S. Pat. No. 3,918,435 to Beall et al., the liquid is provided in a separate frangible container. U.S. Pat. No. 4,175,008 to White additionally provides a long swab stem for ease of specimen taking which includes a breakaway feature for use with a short compact receptacle to facilitate sample transport.

SUMMARY OF THE INVENTION

A liquid recovery device includes a receptacle, a sample transfer means and a wringing means. The transfer means and wringing means are both positioned inside the receptacle, the transfer means below the wringing means.

The preferred receptacle has a body portion, a closed lower end, an open upper end and may additionally have means for removably attaching a cap. The preferred transfer means is a shaft having an absorbent material attached to one end of a shaft. The most preferred receptacle and transfer means are a vial and a swab consisting of a shaft and an absorbent pad.

The wringing means may be any structure adapted to compress the absorbent transfer material and thereby cause removal of a liquid absorbed therein. In one embodiment of the invention, the wringing means is a cap for the receptacle having a hole large enough to allow the shaft to pass through, but small enough so that the absorbent material is compressed when it passes through. Preferably, a flat rubber plug in the cap has a cross slit to facilitate the wringing when the transfer means passes through. Alternatively, the wringing means is a closure inserted into the open upper end of the receptacle. The closure has a passageway therethrough which is dimensioned to compress the absorbent material when it enters the passageway.

In the preferred embodiment of the invention, the wringing means is a sleeve supported within the receptacle. Both ends of the sleeve are open and have closures inserted therein. The closures have aligned passageways through which the shaft passes. The passageways are large enough so that the shaft may be passed through, but small enough so that the absorbent pad is compressed when it enters the passageway in the lower closure.

The cap and wringing means may be an integral unit which includes a sleeve having integrally formed base and head portions with holes therein for the shaft and means such as threads for removable attachment of the integral wringing unit to the receptacle.

In another aspect of the invention, the device may be used in a method for recovering a liquid from an absorbent material. In particular, the device is useful in preparing a sample of an analyte in a small volume of liquid to be used in assaying for the analyte. For example, a swab may be used to take a throat or nasal sample suspected of containing an analyte, such as a microorganism or a virus. The absorbent pad of the swab, having the analyte sample thereon, is mixed thoroughly with a liquid in the receptacle whereby a portion of the liquid is absorbed into the pad. When the swab shaft is pulled upward, the pad enters the hole in the lower closure and is compressed whereby the liquid containing the analyte is squeezed out and collects in the receptacle.

The device of the invention overcomes deficiencies of prior art devices used to collect swab samples and prepare solutions of the samples in a liquid for immunoassay, and, when used in the method of the invention, increases the sensitivity of the immunoassay. Prior art devices make no provision for recovery of the substantial volume of liquid absorbed and retained by the swab. As a result, a larger volume of liquid must be used in prior devices in order to obtain sufficient volumes of solution to carry out the assay. The larger volume reduces the analyte concentration in the solution. The device of the present invention allows recovery of most of the solution which otherwise would be retained by the swab. Smaller volumes of liquid can thus be used, higher concentrations of analyte obtained and more sensitive assays achieved. Further, after wringing, the swab is enclosed in the sleeve thereby providing for safe and sanitary disposal of the used web.

DETAILED DESCRIPTION OF THE INVENTION

While this invention is satisfied by embodiments in many different forms, there will herein be described in detail preferred embodiments of the invention, with the understanding that the present disclosure is to be considered as exemplary of the principles of the invention and is not intended to limit the invention to the embodiments illustrated and described. The scope of the invention will be measured by the appended claims and their equivalents.

The liquid recovery device of the invention comprises a receptacle, a sample transfer unit and a liquid wringing unit. Each of the components will now be described, with the aid of the figures, for a preferred embodiment of the device.

Figures 1, 2, 3, 4, 5:
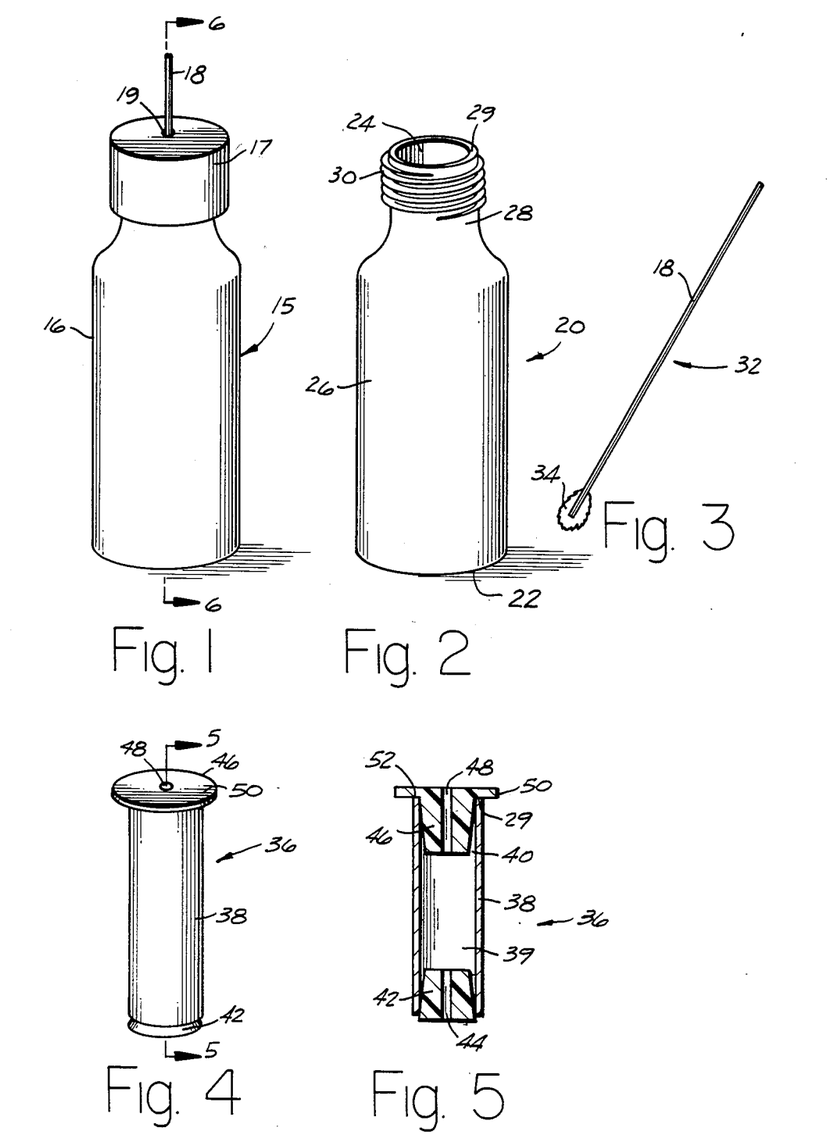
FIG. 1 is perspective view of the liquid recovery device of the invention.
FIG. 2 is a perspective view of a preferred embodiment of the receptacle of the recovery device of FIG. 1.
FIG. 3 is a perspective view of the preferred sample transfer unit of the recovery device of FIG. 1.
FIG. 4 is a perspective view of a preferred wringing unit of the recovery device of FIG. 1.
FIG. 5 is a vertical sectional view of the wringing unit of FIG. 4 taken along the line 5—5 thereof.

FIG. 1 shows liquid recovery device 15 having a receptacle 16, a cap 17 and a shaft 18 of the sample transfer unit passing through a hole 19 in cap 17.

Receptacle 16 has an open upper end and a closed lower end, and in FIG. 2, is depicted as a vial 20 having a closed bottom end 22, an open upper end 24, and a body portion 26. A neck portion 28 of body portion 26 has an upper lip 29 and a thread 30 for removable attachment of cap 17.

The preferred sample transfer unit is a swab 32 having an absorbent pad 34 attached to one end of the shaft 18, as illustrated in FIG. 3. Pad 34 may be attached to shaft 18 in any convenient way provided that the attachment is sufficiently secure to prevent detachment of the pad from the shaft when upward movement (as described below) is applied to shaft 18 and pad 34 is thereby pulled into the wringing unit. A physical means of attachment, such as twisting may be used, or, preferably, a permanent bonding method, such as gluing, may be used.

A preferred embodiment of the wringing unit 36 is illustrated in FIGS. 4 and 5. A sleeve 38 has an open lower end 39 and an open upper end 40. A closure 42 in open lower end 39 has a passageway 44 therethrough. A closure 46 in open upper end 40 has a passageway 48 therethrough and a flange 50. Flange 50 is dimensioned so that its lower edge 52 rests on lip 29 of vial 20, as described below.

Figure 6:
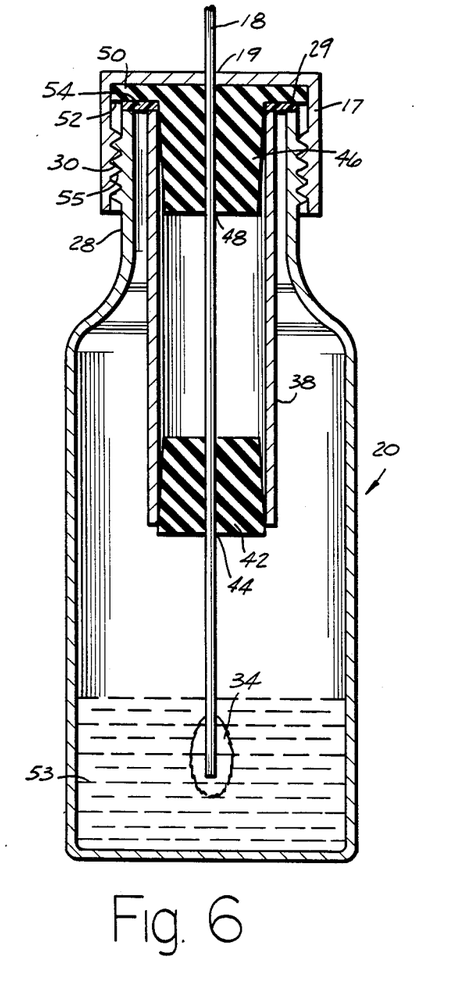
FIGS. 6 is a vertical sectional view of the liquid recovery device of FIG. 1 taken along the line 6—6 thereof.

FIG. 6 shows the relationship of the receptacle, transfer unit and wringing unit in the assembled liquid recovery device of the invention. Absorbent pad 34 attached to shaft 18 is immersed in a reservoir of a liquid 53 in vial 20. Shaft 18 extends through passageways 44 and 48 of closures 42 and 46 respectively. A washer 54 rests on lip 29 of vial neck portion 28 and provides rigidity to support flange 50. Cap 17 has an internal thread 55 which mates with thread 30 of vial neck portion 28.

Figure 7:
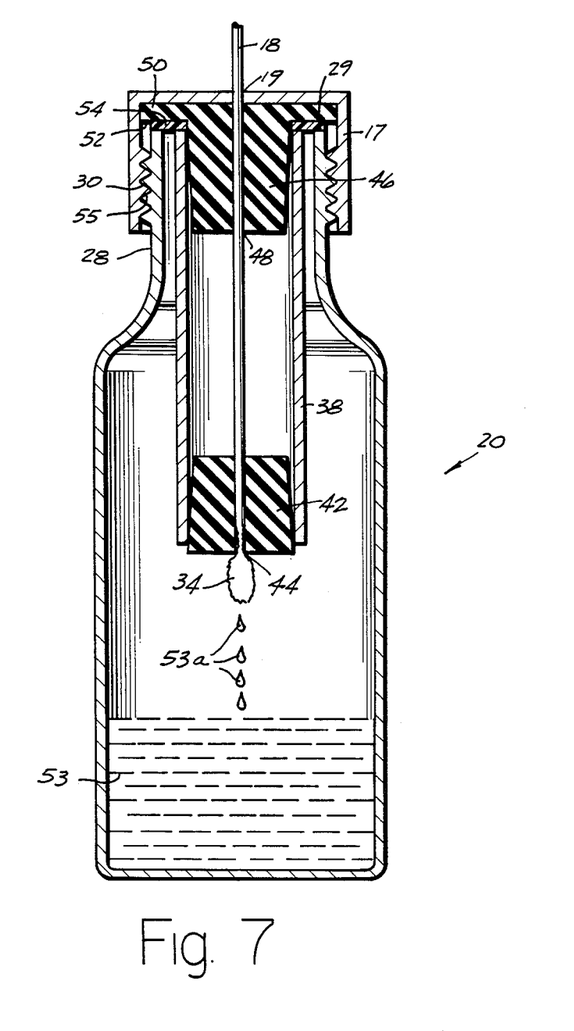
FIGS. 7 and 8 are sectional views similar to FIG. 6 illustrating the sequential steps of removing the swab from the liquid and wringing it.

Pad 34, when withdrawn from liquid 53 by upward movement applied to shaft 18, retains a portion of the liquid due to its absorbent nature. FIG. 7 shows pad 34 entering passageway 44 of lower closure 42. It is seen that passageway 44 is large enough to allow passage of shaft 18 but too small to allow free passage of pad 34. Pad 34 is thereby compressed when in passageway 44 and liquid 53a, retained in the pad, is squeezed out and drips back into the reservoir of liquid 53 in vial 20.

Figure 8:
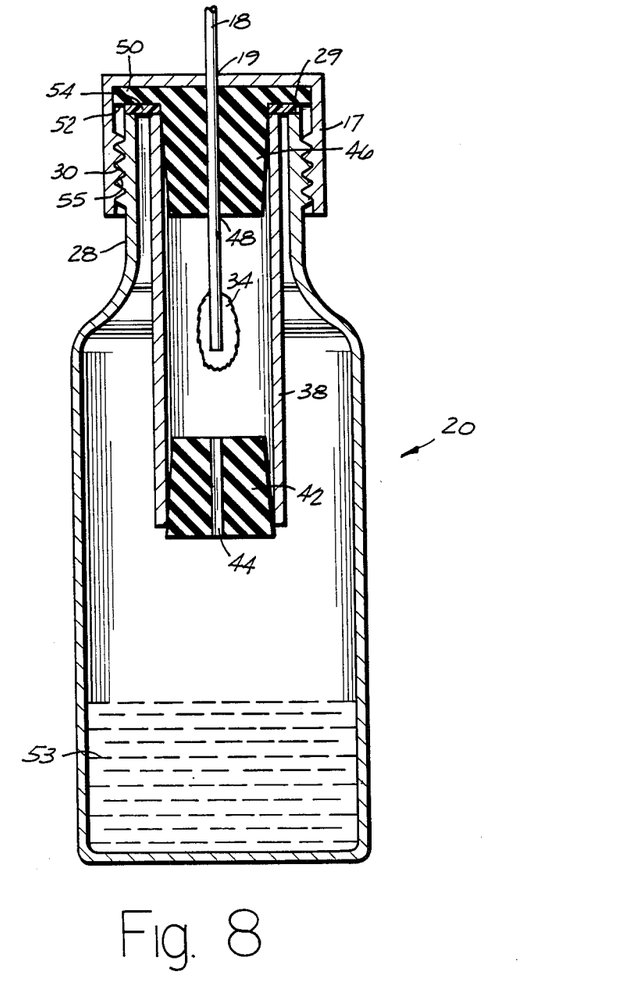

Further upward movement of shaft 18 causes pad 34 to exit from passageway 44 and assume the position in sleeve 38 depicted in FIG. 8. Cap 17 may then be detached from vial 20 by unscrewing threads 30 and 55 and the complete wringing and transfer units including sleeve 38, closure 42 and 46 and shaft 18 with attached pad 34 removed and discarded. Cap 17 may then be replaced, or, preferably, a modified cap (not shown in the figures) identical to 17 in all respects except lacking hole 19, may be used. It is seen that, after removal of the transfer and wringing units and attachment of the modified cap, a sealed vial containing liquid 53 is obtained which is suitable for immediate assay or for storage or transfer. It is further seen that pad 34 is substantially enclosed by sleeve 38 and closures 42 and 46 thereby providing the important advantage of safe and sanitary disposal of the used swab.

Other embodiments of the device are contemplated to fall within the scope of the invention. In the following discussion of alternate embodiments, elements identical or substantially similar to those described above are given the same reference numbers with a letter suffix.

Figure 9:
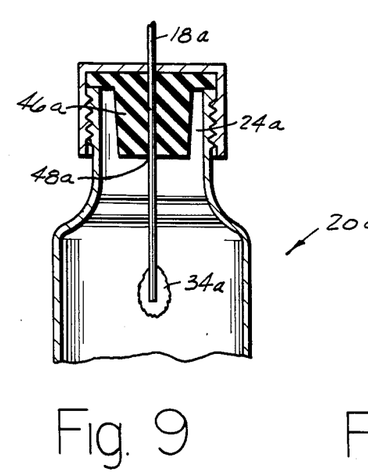
FIG. 9 is a partial vertical sectional view of another embodiment of the recovery device showing an alternative wringing unit.

Sleeve 38, described with respect to the preferred embodiment, may be eliminated and closure 46a placed directly in open end 24a of vial 20a, as shown in FIG. 9. It is seen that wringing will occur when upward movement is applied to shaft 18a so that pad 34a enters passageway 48a.

Figure 10:
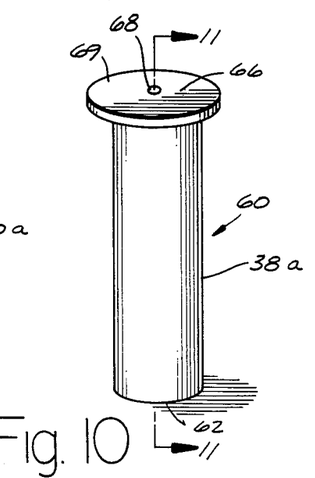
FIG. 10 is a perspective view of an alternative embodiment of the wringing unit.
Figure 11:
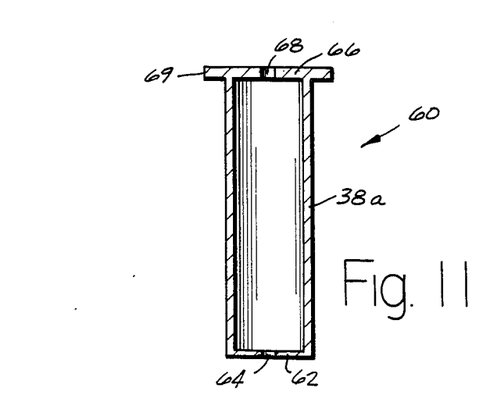
FIG. 11 is a vertical sectional view of the wringing unit of FIG. 10 taken along the line 11—11 thereof.

FIGS. 10 and 11 show wringing unit 60 as an integrally formed unit consisting of sleeve 38a, base portion 62 defining passageway 64 and top portion 66 defining passageway 68. Top portion 66 includes flange 69.

Figure 12:
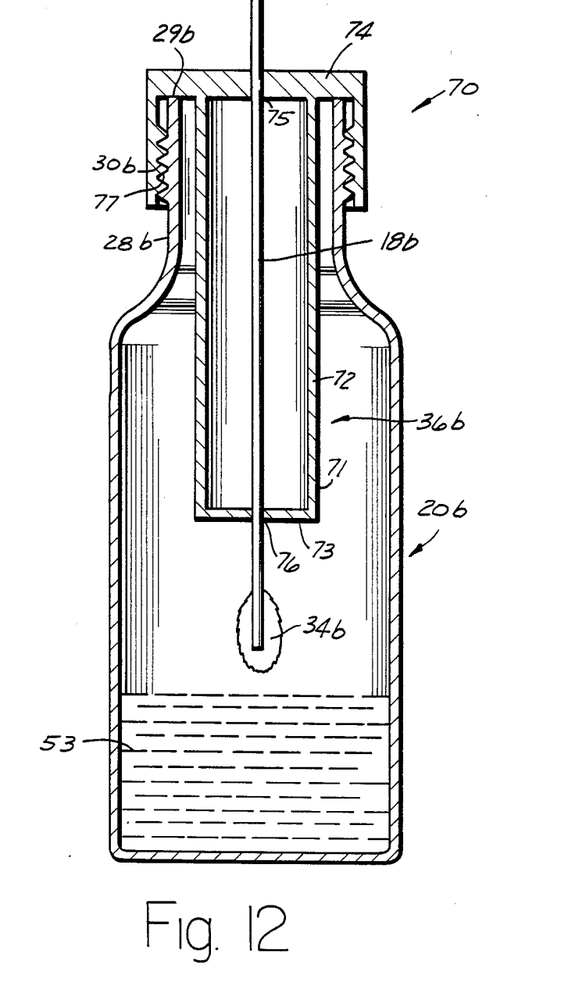
FIG. 12 is a vertical sectional view of a further embodiment of the device showing an integral cap and wringing unit.

An embodiment of the device which includes an integral unit 70 combining the wringing means and cap is illustrated in FIG. 12. Unit 70 has a jacket 71 having a wall portion 72, a base portion 73 and a head portion 74. Head portion 74 rests on and is supported by receptacle lip 29b and defines passageway 75. Base portion 73 defines passageway 76. Shaft 18b slides freely in the passageways. Absorbent pad 34b, when withdrawn from liquid 53 and drawn through passageway 76, is compressed to induce wringing, as described above. Head portion 74 and neck portion 28b of vial 20b have means, illustrated in FIG. 12 as mating threads 30b and 77, for removably attaching the head portion 74 to the vial.

Figure 13:
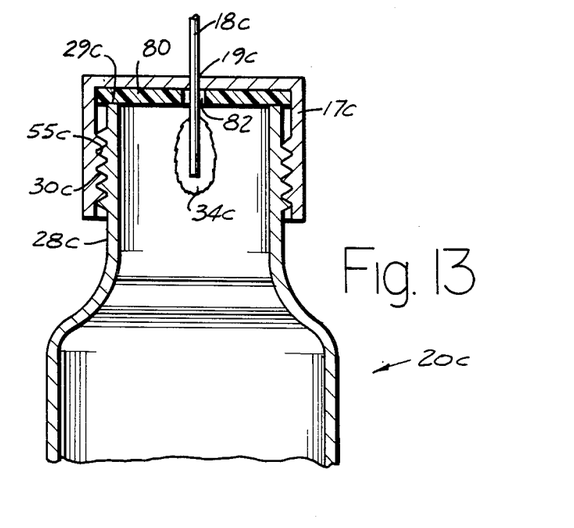
FIGS. 13 and 14 are partial vertical sectional views of alternate embodiments of the recovery device of the present invention.
Figure 14:
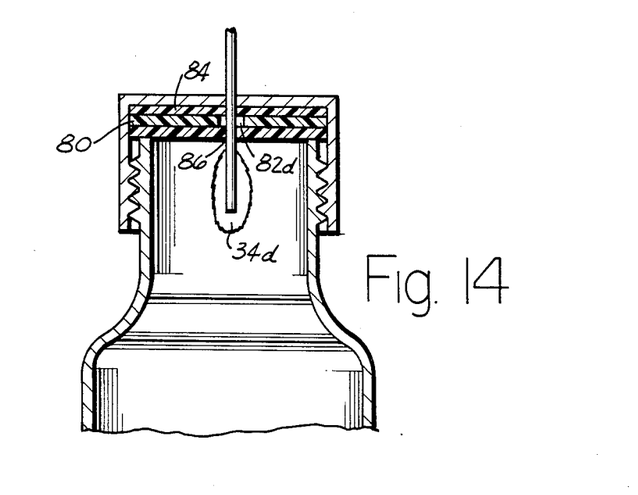

Another embodiment of the invention dispenses entirely with the sleeve and closures. As illustrated in FIG. 13, thread 30c on neck 28c of vial 20c mates with thread 55c of cap 17c. A disc 80, preferably flat, inside of and abutting cap 17c is supported on on lip 29c of neck 28c. Disc 80 has a cross slit 82 in alignment with hole 19c in cap 17c. Shaft 18c having pad 34c thereon passes through hole 19c and cross slit 82. After immersion of pad 34c in a liquid (not shown) in vial 20c, upward movement of shaft 18c draws pad 34c through cross slit 82. Pad 34c is compressed thereby so that absorbed liquid (not shown) is released and falls back into the vial. FIG. 14 shows this embodiment of the device to have an optional flat washer 84 with hole 86 on either or both sides of disc 80 to provide rigidity for prevention of distortion of the disc when pad 34d is drawn through cross slits 82d.

The various embodiments of the liquid recovery device of the invention have been illustrated with threads for attachment of the cap to the vial. It is evident that other means, such as compression or snap fits may be used instead of screw fits.

No criticality is attached to the materials which may be used to construct the various parts of the liquid recovery device of the invention. For example, vial 20 and sleeve 38 may be glass or any suitable plastic, preferably transparent, such as polyolefin, polyurethane and the like. Cap 17 and washer 54, preferably are plastic. Pad 34 may be of any suitable absorbent material, such as glass wool, cotton, rayon, nylon, dacron and the like. Shaft 18 may be plastic or, preferably wood. Closures 42 and 46 and disc 80 may be plastic, preferably rubber.

Vial 20 may contain a reagent, preferably soluble and in lyophilized form, to be reconstituted in liquid 53 when the device is to be used. The reagent may be for any purpose. For example, the reagent may provide a medium to promote growth or maintain the viability of a microorganism, or it may provide a medium for breakdown of material transferred by swab 32 into a form which can more readily be assayed. Alternatively, reagents may be supplied which, when reconstituted in liquid 53, provide a buffer suitable for storing or transporting a material prior to assay.

Any suitable liquid may be added to vial 20 in accordance with the purpose for which the device is to be used. Water or, if desired, an organic solvent may be added. When the device is to be used for immunoassay of an antigen, water, saline, or buffer, and the like may be added.

The volume of liquid to be added to the vial may in general be determined by the use contemplated for the device. Immunoassay procedures in general require from about 5 to 1000 ul of assay solution. Conventional medical swabs retain about 300 ul of liquid, about 200 ul of which may be recovered when the swab is used in conjunction with the device of the invention. Thus, for an assay procedure requiring about 200 ul of antigen solution, only about 300 ul of liquid need be added to the receptacle. On the other hand, conventional preparation of the antigen solution (i.e., without the recovery device of the invention), may require 500 or more ul of liquid to obtain 200 ul of usable antigen solution. Thus, it is seen that the device of the invention provides 40 percent or more increase in antigen concentration in the assay solution and thereby a substantial increase in assay sensitivity.

What is claimed is:

1. A method for recovering liquid from an absorbent material using a receptacle having therein a reservoir of liquid, a sleeve spaced from the liquid and a swab which includes a shaft and an absorbent pad affixed to said shaft, said pad being immersed in the liquid, said swab being constructed and arranged to be removably positioned inside of said receptacle, said sleeve having top and bottom closures within open upper and lower ends of said sleeve, respectively, said top closure having a flange which rests on an upper lip of said receptacle thereby immobilizing said sleeve in said receptacle, said closures having passageways therethrough, said shaft extending through said passageways, said method comprising the steps of:
    (a) applying movement to said shaft whereby said absorbent pad having liqiud absorbed therein emerges from the liquid and enters said passageway through said bottom closure;
    (b) causing said pad to be compressed in the passageway through said bottom closure;
    (c) removing the absorbed liquid from said pad by compressing; and
    (d) collecting liquid removed from said pad in said reservoir.

2. A method for preparing a sample for analysis using a receptacle having therein a liquid, a sleeve spaced from the liquid and a swab which includes a shaft and an absorbent pad affixed to said shaft, said swab being constructed and arranged to be removably positioned inside of said receptacle, said sleeve having top and bottom closures within open upper and lower ends of said sleeve, respectively, said top closure having a flange which rests on an upper lip of said receptacle thereby immobilizing said sleeve in said receptacle, said closures having passageways therethrough, said shaft extending through said passageways, said method comprising the steps of;
    (a) taking a sample to be analyzed on said pad;
    (b) immersing said pad in the liquid whereby the sample and the liquid become mixed and a portion of the liquid containing the sample is absorbed into said pad;
    (c) applying movement to said shaft whereby said pad having the portion absorbed therein emerges from the liquid and enters the passageway through said bottom closure;
    (d) causing said pad to be compressed in the passageway through said bottom closure;
    (e) removing liquid containing the sample from said pad by compressing; and
    (f) collecting liquid removed from said pad in said receptacle.

3. A liquid recovery kit comprising:
    (a) a receptacle having a body portion, a closed bottom and an open top defined by a lip of said body portion;
    (b) a swab having a shaft and an absorbent pad on an end of said shaft, said end and pad being constructed and arranged to be removably positioned inside of said receptacle;
    (c) a jacket within said receptacle, said jacket having integrally formed wall, head and base portions, said head portion having a flange which rests on said receptacle lip and immobilizes said jacket in said receptacle, said means and base portions having aligned holes therein, said shaft extending through said holes, said base portion hole having a size sufficient for said pad to pass therethrough and be compressed thereby; and
    (d) means for removably attaching said head portion to said receptacle.

4. The kit of claim 3 wherein said means for attaching includes threads on said receptacle body portion and on said jacket head portion.

5. A liquid recovery kit comprising:

(a) a receptacle having a body portion, a closed bottom, and an open top defined by a lip of said body portion;

(b) a swab having a shaft and an absorbent pad on an end of said shaft, said end and pad being constructed and arranged to be removably positioned inside of said receptacle; and (c) a sleeve within said receptacle, said sleeve having top and bottom closures within open upper and lower ends of said sleeve, respectively, said top closure having a flange which rests on said lip thereby immobilizing said sleeve in said receptacle, said top and bottom closures having aligned passageways therein, said shaft extending through said passageways, said bottom closure passageway having a size sufficient for said pad to enter therein and be compressed thereby.

6. The kit of claim 5 wherein said top and bottom closures are compressible plugs.

7. The kit of claim 5 wherein said sleeve, top closure and bottom closure are integrally formed.

8. The kit of claim 5 wherein said sleeve and said receptacle are made of a material selected from the group consisting of glass and plastic.

9. The kit of claim 5 wherein said top and bottom closures are made of a material selected from the group consisting of plastic and rubber.

10. The kit of claim 5 wherein said pad is made of a material selected from the group consisting of glass wool, cotton, rayon, dacron and nylon.

11. The kit of claim 5 further comprising a cap removably attached to said receptacle body portion, said cap having a means defining a hole in alignment with said passageways, said shaft extending through said hole.

12. The kit of claim 11 wherein said cap is removably attached to said body portion by mating threads on said cap and body portion.

13. The kit of claim 5 further comprising a reagent in said receptacle.

14. The kit of claim 13 wherein said reagent is a lyophilized reagent in said receptacle

* * * * *